United States Patent [19]

Blake et al.

[11] Patent Number: 5,294,630

[45] Date of Patent: Mar. 15, 1994

[54] TREATMENT OF INFLAMMATORY BOWEL DISEASE

[75] Inventors: David Blake, Droitwich, United Kingdom; Peter P. K. Ho, Carmel; Jill A. Panetta, Zionsville, both of Ind.; David Rampton; Nicola Simmonds, both of London, United Kingdom

[73] Assignees: Eli Lilly and Company, Indianapolis, Ind.; London Hospital Medical College, London, England

[21] Appl. No.: 909,852

[22] Filed: Jul. 7, 1992

[51] Int. Cl.⁵ .......................... A61K 31/425
[52] U.S. Cl. ..................... 514/372; 514/378; 514/380; 514/403; 514/404
[58] Field of Search ............. 514/372, 378, 380, 403, 514/404

[56] References Cited

U.S. PATENT DOCUMENTS

| | | | |
|---|---|---|---|
| 4,346,094 | 8/1982 | Beck et al. | 424/270 |
| 4,495,195 | 1/1985 | Beck et al. | 514/406 |
| 4,544,752 | 10/1985 | Beck et al. | 548/214 |

FOREIGN PATENT DOCUMENTS 513379 11/1991 European Pat. Off. .

OTHER PUBLICATIONS

Salim, *The Amer. J. of the Med. Sciences*, 300(1), 1-6 (1990).
Keshavarzian et al., *Gut.*, 31. 786-790 (1990).
Simmonds et al., *Gastroenterology*, 103(1), 186-196 (1992).
Levin et al., *Dis. Colon Rectum*, 35, 452-456 (1992).
Moyana et al., *Ann. Clin. Lab. Sci.*, 21(4), 258-263 (1991).
Song et al., *Gastroenterology*, 103, A699 (1992).
Fairburn, *The Lancet*, 697-699 (1973).
Wakefield et al., *The Lancet*, 1057-1062 (1989).
Salim, *Digestive Diseases and Sciences* 35(1), 73-79 (1990).
Werns et al., *Circulation*, 83(3), 995-1005 (1991).
Moorhouse, et al., *Febs. Lett.*, 213(1), 23-28 (1987).
Scottile et al., *DICP, The Annals of Pharmacotherapy*, 23, 963-973 (1989).
Shivananda et al., *Scand. J. Gastroenterol.*, 26, 167-173 (1991).
Pavli et al., *Digest Dis.*, 10, 72-84 (1992).
Gibson et al., *Digest Dis.*, 10, 17-28 (1992).

*Primary Examiner*—Leonard Schenkman
*Attorney, Agent, or Firm*—Joseph A. Jones; Leroy Whitaker

[57] ABSTRACT

Inflammatory bowel disease is treated, and patients are protected from a relapse into active disease, by the administration of a compound chosen from a series of 3-phenyl-5-carboxypyrazoles and isothiazoles.

19 Claims, No Drawings

TREATMENT OF INFLAMMATORY BOWEL DISEASE

FIELD OF THE INVENTION

The present invention belongs to the fields of pharmaceutical chemistry and gastroenterology, and provides a method of treating, or preventing the recurrence of, inflammatory bowel disease, and reducing the risk of cancer in inflammatory bowel disease, making use of a series of phenylpyrazoles and phenylisothiazoles.

BACKGROUND OF THE INVENTION

Inflammatory bowel disease (IBD) comprises two conditions, ulcerative colitis (UC) and Crohn's disease (CD). Both UC and CD are chronic inflammatory diseases of the digestive tract, the former restricted to the large intestine and the latter affecting any part of the bowel from mouth to anus. The cause of both diseases is unknown, but increasing evidence points to a major pathogenic role for reactive oxygen metabolites.

The incidence of UC is about 5/100,000/year; that of CD is similar but rising. The prevalence of each disease is about 60/100,000. The diseases first present most commonly in the third decade, with a second peak of incidence at about 60-80 years. Both diseases occur world-wide, but may be more common in developed countries than in the Third World.

The symptoms of each disease are characterized by periods of relapse and remission over many years. The principal symptoms of UC are diarrhea and rectal bleeding. These symptoms may occur in CD of the colon, but when other areas of the bowel are involved, CD tends to cause abdominal pain, weight loss, malaise, fever, and malabsorption as well as diarrhea. In CD more commonly than UC, strictures, fistulas and abscesses within the abdominal cavity may occur. In up to 10 percent of patients with either disease, there may be arthritis, iritis (eye inflammation), skin disorders (erythema nodosum, pyoderma gangrenosum) and liver disease (chronic hepatitis, cirrhosis, sclerosing cholangitis, cancer of the bile duct, amyloid). In chronic UC affecting the whole colon there is an increased risk of colonic cancer.

Medical treatment of UC and CD is similar and at present unsatisfactory. Active relapses are usually treated with corticosteroids (intravenous, orally or topically) with their attendant side-effects. Sulphasalazine and its derivatives (5-aminosalicylic acid) can be used in active disease and are effective in reducing the incidence of relapse in UC; all have occasionally troublesome side effects. Immunosuppressive agents such as azathioprine and 6-mercaptopurine are used in patients not responding to steroids or sulphasalazine and again have adverse effects. When currently available medical therapy fails, surgical resection of affected bowel is necessary, but this is not curative in CD as disease frequently recurs in residual intestine.

The pathogenesis of IBD is presently being studied. There is now increasing evidence that reactive oxygen metabolites (ROM) are important in the pathogenesis of IBD. See Simmonds et al., Chemiluminescent Assay of Mucosal Reactive Oxygen Metabolites in Inflammatory Bowel Disease, *Gastroenterology*, 103 No. 1, to appear in July, 1992. The term ROM is used here to include, particularly, free radicals including superoxide, hydrogen peroxide, hydroxyl and hypochlorite. There is now evidence that ROMs may initiate the inflammatory cascade which leads to IBD. Schreck, Reactive Oxygen Intermediates, as Apparently Widely Used Messengers in the Activation of the NF-KB transcription factor and HIV-1, *EMBO Journal* 10, 2247-58 (1991).

Evidence has been found which demonstrates increased mucosal production of ROMs related to IBD activity, using colorectal biopsies and stimulated mucosal phagocytes. Keshavarzian et al., Excessive Production of Reactive Oxygen Metabolites by Inflamed Colon: Analysis by Chemiluminscence Probe. *Gastroenterology*, 1992, (in press); Williams, Phagocytes, Toxic Oxygen Metabolites and IBD: Implications for Treatment, *Ann. R. Coll. Surg. Engl.*, 72, 253-62 (1990); Simmonds et al., cited above. Further, it has been shown that enough ROMs are produced to cause mucosal damage. Increased lipid peroxides have been found in rectal biopsies of patients with active UC, and 8-oxo-7-hydrodeoxyguanosine, produced by hydroxyl attack on DNA, has been found in the ileocolonic mucosa of patients with CD, as well as in the circulating lymphocytes of patients with UC. Ahnfelt-Ronne et al., Clinical Evidence Supporting the Radical Scavenger Mechanism of 5-aminosalicylic Acid, *Gastroenterology* 98, 1162-69 (1990); Simmonds et al., Reactive Oxygen Metabolites Damage DNA in IBD, abstract submitted to the British Society of Gastroenterology for presentation in September, 1992.

Thus, there is strong evidence that ROMs are instrumental in the pathogenesis of both ulcerative colitis and Crohn's disease, and that the severity of the disease is related to the extent of their over-production. Antioxidant therapy or agents preventing or blocking the formation of ROMs can therefore prove beneficial.

In experimental colitis in animals, specific agents blocking the release or effect of ROMs have been shown to decrease inflammation. E.g., Fretland et al., Superoxide Dismutase Modulates Acetic Acid-Induced Colitis in Rodents. *Gastroenterology* 100, A581 (1991). Studies in man showed promise for the use of allopurinol in pouchitis. Levin et al., Role of Oxygen Free Radicals in the Etiology of Pouchitis, *Dis. Colon Rectum* 35, 452-56 (1992). Superoxide dismutase injections showed promise in refractory CD. Emerit et al., Phase II Trial of CuZnSOD in CD. *Free Radic. Biol. Med.* 7, 145-49 (1989). Furthermore, sulphasalazine and its derivatives may work in IBD, at least in part, by scavenging ROMs. Yamada et al., Antioxidant Properties of 5-Aminosalicylic Acid: Potential Mechanism for its Antiinflammatory Activity. In Williams, Ed., Trends in IBD Therapy, Lancaster: Klumer Acad. Publ., 73-84 (1990); Ahnfelt-Ronne et al., cited above.

There is currently much interest in the relationship between oxidant stress and the development of cancer. Weitzman et al., Inflammation and Cancer: Role of Phagocyte-Generated Oxidants in Carcinogenesis, *Blood* 76, 655-63 (1990). While there is no doubt that ROM can cause oxidative DNA damage leading to base changes, strand breaks, and enhanced expression of proto-oncogenes, and that oxidative stress can induce malignant transformation in cell culture [Halliwell et al., DNA Damage by Oxygen-Derived Species, *FEBS Letters* 281, 9-19 (1991)], the relationship between these observations and the development of malignancy in vivo is more complex and will depend on other factors such as rate of damage, antioxidant defenses, DNA repair mechanisms and the necessity for multiple steps (initiation, promotion and progression). It has been shown that constitutive and oxidant-induced levels of adenosine diphosphate ribosyl transferase (ADPRT), an enzyme involved in DNA repair, are reduced in patients with IBD and also those with colon cancer. Markowitz et al., Hydrogen Peroxide Induced ADPRT Response in Patients with IBD, Gut 29, 1680–86 (1988). It is therefore reasonable that long-term antioxidant therapy in IBD could reduce not only inflammation but also the incidence of colorectal cancer. Pero et al., Oxidative Stress, DNA Repair and Cancer Susceptibility, Cancer Detec. Prev. 14, 555–61 (1990).

There is a clear need for a new potent and safe treatment for the suppression as well as prevention of relapse of IBD. Such treatment might not only improve the bowel disorders themselves, thereby reducing the need for ablative surgery, but also reduce the incidence of the joint, eye, skin and liver complications of IBD.

SUMMARY OF THE INVENTION

The present invention provides a method for treating or preventing the recurrence of inflammatory bowel disease comprising administering to a patient in need thereof an effective dose of a compound of the formula

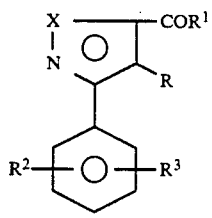

I wherein X is a sulfur atom, a nitrogen atom, or a methyl-substituted nitrogen atom;

R is hydrogen, amino, $C_1$–$C_3$ alkylamino, or hydroxy;
$R^1$ is hydroxy, or OM;
M is a nontoxic cation;
$R^2$ and $R^3$ independently represent hydrogen, halo, $C_1$–$C_3$ alkyl, trifluoromethyl, or $C_1$–$C_3$ alkoxy.

The invention also provides the use of compounds of formula I for treating or preventing the recurrence of inflammatory bowel disease, including preventing colorectal cancer resulting from and in conjunction with IBD, and further provides pharmaceutical formulations which are adapted for that purpose.

DESCRIPTION OF THE PREFERRED EMBODIMENTS

The Compounds

The compounds which are used in the present invention were disclosed by Beck et al. in U.S. Pat. Nos. 4,346,094, 4,495,195 and 4,544,752, all of which are incorporated by reference herein. The nature and synthesis of the compounds are well taught in those patents, and so only a brief discussion is necessary here.

In formula I, the group X can be a sulfur atom, a nitrogen atom or a methyl-substituted nitrogen atom. Thus, since the isothiazole and pyrazole rings are both aryl, that is, fully unsaturated, the location of the double bonds in those rings depends on the nature of the X group, as will be readily understood by the reader. The various possible configurations of that ring are well explained and exemplified in the three Beck et al. patents.

The carboxylic acid group on the pyrazole or isothiazole ring may exist as the acid itself, or as a salt, in which the cation of the salt is represented by M. Pharmaceutical chemists often prepare such drugs as alkali metal salts, wherein M would be sodium, potassium or lithium. M can also be alkaline earth cations such as magnesium or calcium, a nontoxic metal cation such as aluminum or zinc, or an ammonium ion such as piperazinium, butyltrimethylammonium, piperidinium, phenyl-triethylammonium and the like.

The preferred salt-forming moieties include alkali metals and quaternary ammonium groups. More particularly, sodium, potassium, lithium, and quaternary ammonium groups wherein the nitrogen atom is substituted with four hydrogen, $C_1$–$C_{18}$ alkyl, phenyl or benzyl moieties are preferred.

For example, quaternary ammonium groups such as ammonium, tetramethylammonium, diethyl-dimethylammonium, diethyl-dibutylammonium, benzyltrimethylammonium, t-butyl-trimethylammonium, phenyl-triethylammonium, diethyldipropylammonium, s-butyl-trimethylammonium, isobutyltriethylammonium, dimethyl-bis(tetradecyl)ammonium, trimethyl-octadecylammonium, diethyl-decyl-heptadecylammonium and the like are useful and may be chosen for convenience in the circumstances.

A few members of the class of compounds used in this invention will be specifically mentioned, to assure the reader's comprehension.

1-methyl-3-phenyl-4-aminopyrazole-5-carboxylic acid, sodium salt 1-methyl-3-(4-fluorophenyl)-4-aminopyrazole-5-carboxylic acid 1-methyl-3-(3-iodophenyl)pyrazole-5-carboxylic acid, calcium salt 1-methyl-3-(4-methylphenyl)-4-ethylaminopyrazole-5-carboxylic acid, ammonium salt 1-methyl-3-(3-ethylphenyl)-4-hydroxypyrazole-5-carboxylic acid, potassium salt 3-phenyl-4-hydroxypyrazole-5-carboxylic acid, magnesium salt 1-methyl-3-(3-methoxyphenyl)pyrazole-5-carboxylic acid, tetramethylammonium salt 3-(3,4-dimethoxyphenyl)-4-aminopyrazole-5-carboxylic acid, aluminum salt 3-(3-chloro-4-methylphenyl)-pyrazole-5-carboxylic acid, lithium salt 1-methyl-3-(3,4-difluorophenyl)-4-aminopyrazole-5-carboxylic acid 3-(4-trifluoromethyl-3-fluorophenyl)-4-hydroxypyrazole-5-carboxylic acid 3-(4-ethylphenyl)-4-aminopyrazole-5-carboxylic acid, tetraethylammonium salt 3-(4-trifluoromethylphenyl)pyrazole-5-carboxylic acid 1-methyl-3-(3-trifluoromethylphenyl)-pyrazole-5-carboxylic acid 1-methyl-3-(3-trifluoromethylphenyl)-4-propylaminopyrazole-5-carboxylic acid, sodium salt 3-(3-trifluoromethylphenyl)-4-hydroxypyrazole-5-carboxylic acid, ammonium salt 1-methyl-3-(3-trifluoromethylphenyl)-4-aminopyrazole-5-carboxylic acid, potassium salt 3-(3-trifluoromethylphenyl)-4-aminopyrazole-5-carboxylic acid, calcium salt 3-(3-trifluoromethyl-4-chlorophenyl)-4-hydroxypyrazole-5-carboxylic acid 1-methyl-3-(3-trifluoromethyl-5-methoxyphenyl)-4-hydroxypyrazole-5-carboxylic acid, zinc salt 3-(4-fluorophenyl)-4-hydroxyisothiazole-5-carboxylic acid 3-(3-chlorophenyl)isothiazole-5-carboxylic acid, calcium salt 3-(4-methylphenyl)-4-methylaminoisothiazole-5-carboxylic acid, ammonium salt 3-(3-ethylphenyl)-4-hydroxyisothiazole-5-carboxylic acid, potassium salt 3-(3-methoxyphenyl)-4-methylaminoisothiazole-5-carboxylic acid 3-(3,4-dimethoxyphenyl)-4-propylaminoisothiazole-5-carboxylic acid, aluminum salt 3-(3-chloro-4-methylphenyl)isothiazole-5-carboxylic acid, magnesium salt 3-(3,4-difluorophenyl)-4-aminoisothiazole-5-carboxylic acid 3-(4-trifluoromethyl-3-bromophenyl)-4-hydroxyisothiazole-5-carboxylic acid 3-(4-ethylphenyl)-4-aminoisothiazole-5-carboxylic acid, tetraethylammonium salt 3-(4-trifluoromethylphenyl)isothiazole-5-carboxylic acid 3-(3-trifluoromethylphenyl)isothiazole-5-carboxylic acid 3-(3-trifluoromethylphenyl)-4-hydroxyisothiazole-5-carboxylic acid, sodium salt 3-(3-trifluoromethylphenyl)-4-ethylaminoisothiazole-5-carboxylic acid, ammonium salt 3-(3-trifluoromethylphenyl)-4-aminoisothiazole-5-carboxylic acid, potassium salt 3-(4-trifluoromethylphenyl)-4-aminoisothiazole-5-carboxylic acid, calcium salt 3-(3-trifluoromethylphenyl-5-ethylphenyl)-4-aminoisothiazole-5-carboxylic acid 3-(3-trifluoromethylphenyl)-4-hydroxyisothiazole-5-carboxylic acid, magnesium salt 3-(3-trifluoromethyl-4-methoxyphenyl)-4-hydroxyisothiazole-5-carboxylic acid, zinc salt A number of subgroups of the compounds of formula I are particularly preferred for use in the present invention. The following paragraphs list a number of such preferred categories of compounds; it will be understood that the various individual limitations listed below can be combined to create further, more narrowly limited groups of compounds.

a) X is a sulfur atom;
b) X is a nitrogen atom;
c) X is a methyl-substituted nitrogen atom;
d) R is hydrogen or amino;
e) R is amino or alkylamino;
f) R is hydroxy or hydrogen;
g) $R^1$ is hydroxy;
h) $R^1$ is OM;
i) M is a metal ion;
j) M is an ammonium ion;
k) one and only one of $R^2$ and $R^3$ is hydrogen;
l) $R^2$ and $R^3$ independently represent hydrogen, halo or trifluoromethyl;
m) $R^2$ is hydrogen and $R^3$ is trifluoromethyl;
n) $R^2$ and $R^3$ independently represent hydrogen, alkyl or alkoxy.

The methods of synthesis of the compounds used in the present invention are taught by Beck et al. in the above-mentioned patents, to which the skilled reader can easily refer.

OPERATING EXAMPLE

The presence and activity of ROMs in tissue affected by ulcerative colitis and Crohn's disease have been successfully measured by a chemiluminescence assay, making use of 300 μM lucigenin to amplify the chemiluminescence. See Simmonds et al., *Gastroenterology*, cited above. The assay method was validated by measuring the chemiluminescence observed in tissues exhibiting various degrees of UC or CD against the chemiluminescence observed in normal tissues. In the normal tissues, the median chemoluminescence measurement was about 8,000 photons/minute/mg wet weight. The median chemiluminescence measurements in tissues from patients with active, severe IBD, increased to as much as about 90,000 on the same scale.

The effect of the compounds of the present invention was demonstrated by adding a $10^{-6}$ molar concentration of 3-(3-trifluoromethylphenyl)-4-aminoisothiazole-5-carboxylic acid to the buffer in which samples of tissue from UC patients was maintained. It was observed that the addition of the compound inhibited the production of chemiluminescence by from 8% to 70%, with a median inhibition of about 25%, indicating a corresponding reduction in the presence or activity, or both of the reactive oxygen metabolites in the tissue.

Compositions and Methods of Use

The treatment methods of the present invention are useful and beneficial to all patients suffering from inflammatory bowel disease, including patients with ulcerative colitis and those suffering from Crohn's disease. Both patients who are suffering from an active outbreak of IBD and those who have suffered from active IBD, but are presently in a state of remission, are benefited by the present treatment methods Thus, it is clear that the present method includes both therapeutic methods, for the treatment of actively suffering patients, and prophylactic methods, for the prevention of the relapse of patients who are at risk of IBD in any of its forms, but who are presently in a state of remission.

The general routes of administration by which the compounds are effective, and some information about the formulations of them, are taught in the Beck et al. patents, cited above. In the case of administration for the treatment of IBD, oral administration of the drug is usually preferable, because of the convenience and economy of such administration. The compounds may be formulated for oral administration in the usual pharmaceutical forms, such as tablets, capsules, suspensions, solutions and the like. The compounds may also be administered intravenously, intramuscularly or even transdermally, if it is particularly convenient to do so, for example, for patients who are so ill that they cannot take drugs orally.

In the instance of patients whose IBD is only or primarily affecting the rectum and distal colon, the compounds may be administered topically, as in the forms of suppositories or enemas, in order to place the drug in immediate contact with the affected tissues.

It will be understood, however, that the present methods of treatment may not be effective, or will be only partially effective, in patients whose ulcerative colitis or Crohn's disease has advanced to the point that there are major structural (fistula) or infective (abscess) complications. Such patients may be only amenable to surgical intervention to take care of the major complications, but, even in such a case, treatment with the present methods will alleviate the disease in those tissues in which the disease has not progressed to the point of major complication.

The preparation of oral and parenteral formulations of the present compounds were clearly taught by Beck et al., and need not be discussed further. However, topically administered formulations of the compounds for IBD are quite different, and have not previously been disclosed. Such compositions are adapted to be administered rectally. In general, such formulations are in the liquid form administered as enemas and in the solid form administered as suppositories. Both formulation types are old in the pharmaceutical art and the formulation of the present compounds in such forms presents no unusual difficulties.

Suppositories, in general, are usually prepared from low-melting solid materials, which are administered in the solid form and melt in the rectum, to release the drug which is dispersed in the solid matrix. Traditionally, the solids from which suppositories were made were oily or waxy materials, such as cocoa butter and the like. Bland petroleum and vegetable waxes have also been used, as have mixtures of vegetable oils thickened with such waxes. The availability of gelling agents in modern chemistry enables such formulations to be prepared in aqueous-based materials, avoiding the administration of oily and waxy materials, which, of course, are quite foreign to the body. Such an aqueous-based suppository can be prepared by dissolving or suspending the drug in water, preferably made isotonic by addition of appropriate inorganic salts, and thickening the mixture by the addition of a gelling agent such as a carboxycellulose, for example, until it has become a soft solid at room temperature but will liquify at the temperature of the body. The problem of balancing the melting temperature of suppositories is easily reduced, of course, by labelling the product to be stored under refrigeration.

When the drug is to be administered as an enema, it need only be dissolved or dispersed in a small volume, such as 100 ml or less, of an aqueous mixture. It is preferable to make the mixture isotonic, to avoid any upset in the water balance of the affected tissues. Thus, the vehicle for an enema may be no more complicated than physiological buffered saline. It may be convenient to prepare an enema mixture as a solid, comprising a dose of the drug with appropriate quantities of the buffering salts, to be reconstituted with deionized water at the time of use. Alternatively, if an easily water-soluble salt of the drug is chosen, the appropriate dose of the drug may simply be dissolved in physiological buffered saline and administered in that form.

The dose of drug to be administered in the practice of the present methods of treatment must be chosen by the attending physician, taking into account the severity of the patient's IBD, the extent of involvement of tissues, and the potency of the specific drug which is chosen. In general, it will be necessary to administer a larger dose if the administration is systemic, such as oral or parenteral, then if a topical administration directly to the affected tissue is chosen. An appropriate range of doses is from about 1 to 100 mg/kg., particularly for systemic administration. When topical administration is used, a more appropriate range of doses is from about 0.2 to about 40 mg/kg. A more preferred range of doses, however, is from about 2 to about 50 mg/kg, and a still more preferred dosage range is from about 5 to about 35 mg/kg.

FORMULATION EXAMPLES

The following examples illustrate the types of topical compositions which may be used to administer drugs in the present methods of treatment.

EXAMPLE 1

3-(3-trifluoromethylphenyl)-4-aminopyrazole-5-carboxylic acid, sodium salt
Quantity: 100 mg
Physiological buffered saline
Quantity: 100 ml
Dissolve the drug in the saline for use as an enema solution.

EXAMPLE 2

1-methyl-3-(3,4-difluorophenyl)-4-aminopyrazole-5-carboxylic acid
Quantity: 500 mg
Deionized water: 50 ml
Disperse the drug in the water for use as an enema mixture.

EXAMPLE 3

3-(3-chloro-4-methylphenyl)isothiazole-5-carboxylic acid
tetraethylammonium salt: 200 mg
Physiological buffered saline: 100 ml
Dissolve the drug in the saline for administration as an enema.

EXAMPLE 4

3-(3-trifluoromethylphenyl)-4-hydroxyisothiazole-5-carboxylic acid
magnesium salt: 300 mg
Cocoa butter, 3 g
Disperse the drug smoothly through the cocoa butter and form into a suppository.

EXAMPLE 5

3-(4-methylphenyl)-4-methylaminoisothiazole-5-carboxylic acid
ammonium salt: 500 mg
Gelled glycerine, 5 g
Dissolve the drug in the gelled glycerine and form into a suppository.

EXAMPLE 6

3-(4-methoxyphenyl)-4-methylaminoisothiazole-5-carboxylic acid, phenyl-trimethyl
ammonium salt: 100 mg
Alginate gel: 2 g
Disperse the drug in the alginate gel and form into a suppository.

We claim:
1. A method for treating or preventing the recurrence of inflammatory bowel disease comprising administering to a patient in need thereof an effective dose of a compound of the formula

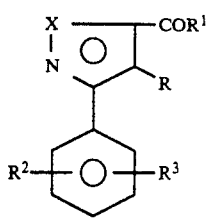

wherein X is a sulfur atom, a nitrogen atom, or a methyl-substituted nitrogen atom;
R is hydrogen, amino, $C_1$–$C_3$ alkylamino, or hydroxy;
$R^1$ is hydroxy, or OM;
M is a nontoxic cation;
$R^2$ and $R^3$ independently represent hydrogen, halo, $C_1$–$C_3$ alkyl, trifluoromethyl, or $C_1$–$C_3$ alkoxy.

2. A method of claim 1 wherein the disease is ulcerative colitis.

3. A method of claim 1 wherein the disease is Crohn's disease.

4. A method of claim 1 wherein the compound is a compound wherein X is a sulfur atom.

5. A method of claim 2 wherein the compound is a compound wherein X is a sulfur atom.

6. A method of claim 3 wherein the compound is a compound wherein X is a sulfur atom.

7. A method of claim 4 wherein the compound is a compound wherein R is hydrogen or amino.

8. A method of claim 4 wherein the compound is a compound wherein $R^2$ and $R^3$ independently represent hydrogen, halo or trifluoromethyl.

9. A method of claim 8 wherein the disease is ulcerative colitis or Crohn's disease.

10. A method of claim 9 wherein the compound is 3-(3-trifluoromethylphenyl)-4-aminoisothiazole-5-carboxylic acid or a salt thereof incorporating a non-toxic cation.

11. A suppository or enema mixture formulation adapted for rectal administration comprising an effective amount of a compound of the formula

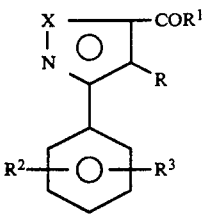

wherein X is a sulfur atom, a nitrogen atom, or a methyl-substituted nitrogen atom;
R is hydrogen, amino, $C_1$–$C_3$ alkylamino, or hydroxy;
$R^1$ is hydroxy, or OM;
M is a nontoxic cation;
$R^2$ and $R^3$ independently represent hydrogen, halo, $C_1$–$C_3$ alkyl, trifluoromethyl, or $C_1$–$C_3$ alkoxy.

12. A formulation of claim 11 which is an enema mixture.

13. A formulation of claim 11 which is a suppository.

14. A formulation of claim 11 wherein the compound is a compound wherein $R^2$ and $R^3$ independently represent hydrogen, halo or trifluoromethyl.

15. A formulation of claim 11 wherein the compound is a compound wherein X is a sulfur atom.

16. A formulation of claim 14 wherein the compound is a compound wherein X is a sulfur atom.

17. A formulation of claim 16 wherein the compound is 3-(3-trifluromethylphenyl)-4-aminoisothiazole-5-carboxylic acid or a salt thereof incorporating a non-toxic cation.

18. A formulation of claim 17 which is an enema mixture.

19. A formulation of claim 17 which is a suppository.

* * * * *